(12) United States Patent
Shibatani et al.

(10) Patent No.: US 7,547,819 B2
(45) Date of Patent: Jun. 16, 2009

(54) PLANT PRODUCING HYALURONIC ACID

(75) Inventors: Shigeo Shibatani, Otsu (JP); Shuhei Misawa, Tsuruga (JP); Izumi Ihara, Otsu (JP); Hiroaki Kitazawa, Otsu (JP)

(73) Assignee: Toyo Boseki Kabushiki Kaisha, Osaka-Shi (JP)

( * ) Notice: Subject to any disclaimer, the term of this patent is extended or adjusted under 35 U.S.C. 154(b) by 0 days.

(21) Appl. No.: 10/566,157

(22) PCT Filed: Jul. 30, 2004

(86) PCT No.: PCT/JP2004/011306

§ 371 (c)(1),
(2), (4) Date: Jan. 27, 2006

(87) PCT Pub. No.: WO2005/012529

PCT Pub. Date: Feb. 10, 2005

(65) Prior Publication Data

US 2006/0168690 A1  Jul. 27, 2006

(30) Foreign Application Priority Data

Jul. 31, 2003 (JP) ............................. 2003-204896
Mar. 25, 2004 (JP) ............................. 2004-089135

(51) Int. Cl.
*C12N 15/33* (2006.01)
*C12N 15/52* (2006.01)
*C12N 15/63* (2006.01)
*C12N 15/83* (2006.01)
*A01H 5/00* (2006.01)

(52) U.S. Cl. ................. 800/280; 800/288; 800/287; 800/298; 435/320.1; 435/468; 536/23.1; 536/23.72

(58) Field of Classification Search .............. 435/6, 435/69.1, 468, 419, 252.3, 320.1; 530/370; 536/23.7; 800/278, 295, 320

See application file for complete search history.

(56) References Cited

U.S. PATENT DOCUMENTS

| | | | | |
|---|---|---|---|---|
| 4,801,539 | A * | 1/1989 | Akasaka et al. | 435/101 |
| 5,985,668 | A * | 11/1999 | Mattes et al. | 435/471 |
| 6,147,280 | A * | 11/2000 | Smeekens et al. | 800/284 |
| 6,395,965 | B1 * | 5/2002 | Xia | 800/295 |
| 6,444,805 | B1 * | 9/2002 | Sohn et al. | 536/23.72 |
| 6,991,921 | B2 * | 1/2006 | Weigel et al. | 435/84 |

FOREIGN PATENT DOCUMENTS

| JP | 2001-521741 | 11/2001 |
|---|---|---|
| WO | 99 23227 | 5/1999 |
| WO | PCT/US 98/23153 | 5/1999 |

OTHER PUBLICATIONS

DeAngelis, et al., (1997) Science 278:1800-1803.*
Sweetlove et al., (1996) Starch Metabolism In Tubers Of Transgenic Potato (Solanum Tuberosum) With Increased ADP-Glucose Pyrophosphorylase. Biochem J. 30:493-98.*
Sutton et al, (1992) Transgenic research, vol. 1, No. 5, pp. 228-236.*
Bornke (2002) Planta 214:356-364.*
Broun et al, 1988, Science 282:1315-1317.*
Fischer et al 2000 Transgenic Research 9:279-299.*
Supplementary European Search Report 04 77 1309, Jul. 26, 2006.
P.L. DeAngelis, "Hyaluronam synthases: fascinating glycosyltransferases from vertebrates, bacterial pathogens, and algal viruses", CMLS Cellular and Molecular Life Sciences, vol. 56, pp. 670-682, 1999.
Shyjan A.M. et al., "Functional Cloning f the CDNA for a Human Hyaluronan Synthase", Journal of Biological Chemistry American society of Biolochemical Biologists, vol. 271, No. 38, Sep. 20, 1996, pp. 23395-23399.
Spicer A.P., et al., "Molecular Cloning and Characterization of a CDNA Encoding Third Putative Mammalian Hyaluronan Synthase", Journal of Biological Chemistry American Society of Biolochemical Biologists, vol. 272, No. 14, Apr. 4, 1997, pp. 8957-8961.
Graves M.V. et al., Hyaluronan Synthesis in Virus PBCV-1-Infected Chlorella-Like Green Algae, Virology, 1999, vol. 257, No. 1, pp. 15-23.
Deangleis, P.L. et al., Hyaluronan Synthase of Chlorella Virus PBCV-1, Science, 1997, vol. 278, No. 5344, pp. 1800-1803.
International Search Report PCT/JP2004/011306, Completed Sep. 29, 2004.

* cited by examiner

*Primary Examiner*—Anne Marie Grunberg
*Assistant Examiner*—Brent Page
(74) *Attorney, Agent, or Firm*—Kenyon & Kenyon LLP

(57) ABSTRACT

The invention relates to a method of producing hyaluronic acid including (1) a step of transforming a plant cell using an expression recombinant vector including (i) a DNA encoding hyaluronic acid synthase or (ii) a DNA encoding a polypeptide having an amino acid sequence having one or more amino acid deletions, substitutions, additions or insertions in an amino acid sequence of the hyaluronic acid synthase and having an activity of synthesizing the hyaluronic acid, (2) a step of growing a transformant obtained by transformation, and (3) a step of separating the hyaluronic acid produced by the transformant.

11 Claims, 1 Drawing Sheet

SEQUENCE LISTING

<160> NUMBER OF SEQ ID NOS: 6

<210> SEQ ID NO 1
<211> LENGTH: 1707
<212> TYPE: DNA
<213> ORGANISM: Chlorella virus

<400> SEQUENCE: 1

```
atgggtaaaa atataatcat aatggtttcg tggtacacca tcataacttc aaatctaatc      60
gcggttggag gagcctctct aatcttggct ccagcaatta ctgggtatat tctacattgg     120
aatattgctc tctcgacaat ctggggagta tcagcttatg gtattttcgt ttttggtttt     180
ttccttgcac aagtttatt ttcagaactg aacaggaaac gtcttcgcaa gtggatttct     240
ctcagaccta agggttggaa tgatgtccgt ttggctgtga tcattgctgg ataccgcgaa     300
gatccctata tgttccaaaa gtgtctcgag tcagtgcgtg actctgacta cggtaacgtt     360
gctcgtctca tttgtgttat tgacggcgat gacgacgctg atatgaagat gtccgatgtt     420
tacaagacga tctacaacga taatatcaag aagcccgagt ttgtcttgtg tgagtcagac     480
gacaaggaag gtgaacgcat cgactctgat ttctctcgcg acatttgtgt tctccagcct     540
caccgtggca agagggagtg tctctatact ggtttccaac ttgcaaagat ggaccccagt     600
```

```
gtcaacgccg tcgttttgat tgacagcgat actgttctcg agaaggatgc tattctggaa    660
gttgtatacc cacttgcatg cgatcctgag atccaagccg tcgcaggtga gtgtaagatt    720
tggaacacag acactctttt gagtcttctc gtcgcttggc ggtactattc tgcgttttgt    780
gtggagagga gtgcccagtc ttttttcagg actgttcagt gcgttggggg cccgctgggt    840
gcctacaaga ttgatatcat taaggagatt aaggacccct ggatttccca gcgctttctt    900
ggtcagaagt gtacttacgg tgacgaccgc cggctaacca acgagatctt gatgcgtggt    960
aaaaaggttg tgttcactcc atttgctgtt ggttggtctg acagtccgac caatgtgttt   1020
cgatacatcg ttcagcagac ccgctggagt aagtcgtggt gccgcgaaat tggtacacc    1080 ctcttcgccg cgtggaagca cggttttgtct ggaatttggc tggcctttga atgtttgtat   1140
caaattacat acttcttcct cgtgatttac ctctttttctc gcctagccgt tgaggccgac   1200
cctcgctccc agacagccac agtgattgtg agcaccacgg ttgcattgat taagtgtggg   1260
tatttttcat tccgagccaa ggatattcgg gcttttttact ttgtgcttta tacatttgtt   1320 tacttttttct gtatgattcc ggccaggggtt actgcaatga tgacgctttg ggacattggc   1380
tggggtactc gcggtggaaa cgagaagcct tccgttggca cccgggtcgc tctgtgggca   1440
aagcaatatc tcattgcata tatgtggtgg gccgcggttg ttggcgctgg agtttacagc   1500
atcgtccata actggatgtt cgattggaat tctctttctt atcgttttgc tttggttggt   1560
atttgttctt acattgtttt tattactatt gtgctggtga tttatttcac cggcaaaatt   1620
acgacttgga atttcacgaa gcttcagaag gagctaatcg aggatcgtgt tctgtacgat   1680
gcatctacca atgctcagtc tgtgtga                                       1707

<210> SEQ ID NO 2
<211> LENGTH: 1707
<212> TYPE: DNA
<213> ORGANISM: Chlorella virus

<400> SEQUENCE: 2
atgggtaaaa atataatcat aatggtttcg tggtacacca tcataacttc aaatctaatc     60
gcggttggag gagcctctct aatcttggct ccagcaatta ctggatatat tctacattgg    120
aatattgctc tctcgacaat ctggggagta tcagcttatg gtattttcgt ttttggtttt    180
ttccttgcac aagttttatt ttcagaactg aacaggaaac gtcttcgcaa atggatttct    240
ctcagaccta agggttggaa tgatgtccgt ttggctgtga tcattgctgg ataccgcgaa    300
gatccctata tgttccaaaa gtgtctcgag tcagtgcgtg actctgacta cggtaacgtt    360
gctcgtctca tttgtgttat tgacggcgat gacgacgctg atatgaagat gtccgatgtt    420
tacaagacga tctacaacga taatatcaag aagcccgagt ttgtcttgtg tgagtcagac    480
gacaaggaag tgaacgcat cgactctgat ttctctcgcg acatttgtgt tctccagcct    540
caccgtggca agagggagtg tctctatact ggtttccaac ttgcaaagat ggaccccagt    600
gtcaacgccg tcgttttgat tgacagcgat actgttctcg agaaggatgc tattctggaa    660
gttgtatacc cacttgcatg cgatcctgag atccaagccg tcgcaggtga gtgtaagatt    720
tggaacacag acactctttt gagtcttctc gtcgcttggc ggtactattc tgcgttttgt    780
gtggagagga gtgcccagtc ttttttcagg actgttcagt gcgttggggg cccgctgggt    840
gcctacaaga ttgatatcat taaggagatt aaggacccct ggatttccca gcgctttctt    900
ggtcagaagt gtacttacgg tgacgaccgc cggctaacca acgagatctt gatgcgtggt    960
```

-continued

```
aaaaaggttg tgttcactcc atttgctgtt ggttggtctg acagtccgac caatgtgttt      1020
cgatacatcg ttcagcagac ccgctggagt aagtcgtggt gccgcgaaat ttggtacacc      1080
ctctttgccg cgtggaagca cggttttgtct ggaatttggc tggcctttga atgtttgtat    1140
caaattacat acttcttcct cgtgatttac ctctttttctc gcctagccgt tgaagccgac    1200
cctcgctccc agacagccac agtgattgtg agcaccacgg ttgcattgat taagtgtggg    1260 tattttttcat tccgagccaa ggatattcgg gcttttttact ttgtgcttta tacatttgtt  1320 tacttttttct gtatgattcc ggccagggtt actgcaatga tgacgctttg ggacattggc   1380
tggggtactc gcggtggaaa cgagaagcct tccgttggca cccgggtcgc tctgtgggca    1440
aagcaatatc tcattgcata tatgtggtgg gccgcggttg ttggcgctgg agtttacagc    1500
atcgtccata actggatgtt cgattggaat tctctttctt atcgttttgc tttggttggt     1560
atttgttctt acattgtttt tattactatt gtgctggtga tttatttcac cggcaaaatt     1620
acgacttgga atttcacgaa gcttcagaag gagctaatcg aggatcgtgt tctgtacgat    1680
gcatctacca atgctcagtc tgtgtga                                         1707
```

<210> SEQ ID NO 3
<211> LENGTH: 40
<212> TYPE: DNA
<213> ORGANISM: Artificial Sequence
<220> FEATURE:
<223> OTHER INFORMATION: primer

<400> SEQUENCE: 3
gccgccgcat atgggtaaaa atataatcat aatggtttcg      40

<210> SEQ ID NO 4
<211> LENGTH: 36
<212> TYPE: DNA
<213> ORGANISM: Artificial Sequence
<220> FEATURE:
<223> OTHER INFORMATION: primer

<400> SEQUENCE: 4
cttgcagtct agatcacaca gactgagcat tggtag      36

<210> SEQ ID NO 5
<211> LENGTH: 36
<212> TYPE: DNA
<213> ORGANISM: Artificial Sequence
<220> FEATURE:
<223> OTHER INFORMATION: primer

<400> SEQUENCE: 5
gtgtggaatt taaagcggat aacaatttca cacagg      36

<210> SEQ ID NO 6
<211> LENGTH: 24
<212> TYPE: DNA
<213> ORGANISM: Artificial Sequence
<220> FEATURE:
<223> OTHER INFORMATION: primer

<400> SEQUENCE: 6
gggcgaattg gagctccacc gcgg      24

PLANT PRODUCING HYALURONIC ACID

This is a 371 national phase application of PCT/JP2004/011306 filed 30 Jul. 2004, claiming priority to Japanese Patent Application No. 2003-204896 filed 31 Jul. 2003, and No. 2004-089135 filed 25 Mar. 2004, the contents of which are incorporated herein by reference.

TECHNICAL FIELD

The present invention primarily relates to a method of producing hyaluronic acid (or hyaluronan or hyaluronate; HA) by plants, transformed plant cells or transformed plants having an ability of producing the hyaluronic acid, and methods of production thereof.

BACKGROUND ART

A plant is an ideal system for producing carbohydrates with low energy load, in which carbohydrates are photosynthetically produced from water and carbon dioxide. Except for a part of organisms, the other organisms can not synthesize the carbohydrates by themselves and utilize the sugars derived from the plants. Meanwhile, each of an animal and a microorganism inherently has the ability to synthesize the carbohydrates by modifying the sugars and extending sugar chains using the sugars derived from the plants as sources, and there are sugar derivatives and carbohydrates derived from the animals and the microorganisms, which the plants can not produce. The carbohydrate which can not be produced in the plants and is produced by the animals and the microorganisms includes hyaluronic acid.

The hyaluronic acid is glycosaminoglycan (mucopolysaccharide) isolated from corpus vitreous body from bovine eye ball by Meyer and Palmer in 1934 (Meyer, K. and Palmer, J. W. (1934) J. Biol. Chem., 107, 629-634). They have demonstrated that this substance is a linear polysaccharide of repeating glucuronic acid $\beta$-1,3-N-acetylglucosamine $\beta$-1,4 disaccharide units (Weissman, B. and Meyer, K. (1954) J. Am. Chem. Soc., 76, 1753-1757).

Subsequently in 1950s to 1960s, the study on biosynthesis of the hyaluronic acid was performed by a cell-free system from Group A *Streptococcus*. The streptococcal enzyme activity localized on the membrane fraction was shown by using two sugar nucleotides of uridine-5'-diphosphoglucuronic acid (sometimes referred to as UDP-glucuronic acid or UDP-GlcA) and uridine-5'-diphospho-N-acetylglucosamine (sometimes referred to as UDP-N-acetylglucosamine or UDP-GlcNAc) in production of a hyaluronic acid chain (Markovitz, M., Cifonelli, J. A. and Dorfman, A. (1959) J. Biol. Chem., 234, 2343-2350). It had been difficult for a long time to solubilize and highly purify the hyaluronic acid synthase as a stable active form, but a gene (hasA) encoding the streptococcal hyaluronic acid synthase was cloned in 1993 (DeAngelis, P. L., Papaconstantinou, J. and Weigel, P. H. (1993) J. Biol. Chem., 268, 14568-14571). Since then, clonings of the genes encoding the hyaluronic acid synthase in mammalian cells were reported (Itano, N. and Kimata, K. (1996) J. Biol. Chem., 271, 9875-9878; Itano, N. and Kimata, K. (1996) Biochem. Biophys. Res. Commun., 222, 816-820; Spicer, A. P., Augustine, M. L. and McDonald, J. A (1996) J. Biol. Chem., 271, 23400-23406; Spicer, A. P., Olson, J. S. and McDonald, J. A. (1997) J. Biol. Chem., 272, 8957-8961; Shyjan A. M., Heldin, P., Butcher E. C., Yoshino T. and Briskin, M. J. (1996) J. Biol. Chem., 271, 23395-23399; Watanabe, K. and Yamaguchi, Y. (1996) J. Biol. Chem., 271, 22945-22948), further the genes encoding the hyaluronic acid synthase in chlorella virus PBCV-1 (DeAngelis, P. L., Jing, W. Graves, M. V., Burbank, D. E. and vam Etten, J. L. (1998) Science, 278, 1800-1804) and *Passteurella multocida* (DeAngelis, P. L., Jing, W. Drake, R. R. and Achyuthan, A. M. (1998) J. Biol. Chem., 273, 8454-8458) have been found, and recombinant enzymes of the active form have been obtained.

Along with advance of these studies, physiological functions of the hyaluronic acid have been widely elucidated, and unique physicochemical properties and biological functions thereof have been demonstrated. High molecular weight hyaluronic acid has been used for the treatment of arthrosis deformans, a surgery aid for ophthalmology, adhesion prevention and acceleration of wound healing. It has been also reported that low molecular weight hyaluronic acid has physiologically active effects, and the application thereof to biomaterials and new medical uses has been anticipated.

Until now, the hyaluronic acid has been produced by extraction from mammalian tissues or microbial fermentation. However, risk of contamination with, for example, transmissible spongiform encephalopathies (prions) or transmission of viruses to humans has been concerned in the extraction from the mammalian tissues. For mammalian cells, maintenance thereof is difficult and requires expensive media, and additionally, a growth rate thereof is slow. Meanwhile for the microbial fermentation, the media containing the sugars and cost for equipment investment are problematic. In *Escherichia coli*, processing of a protein does not occur, it is likely that inclusion bodies are formed and a product is degraded by protease, which are problematic (Petrides, D. et al. (1995) Biotecnol. Bioeng., 48, 529). When the therapeutic substance is produced in the microorganism, the purification cost becomes extremely expensive in order to prevent endotoxin from contaminating.

From these results, if the source sugars are produced in the plants by photosynthesis and the hyaluronic acid can be produced in the plants using such sugars, it appears to be industrially advantageous in terms of safety and cost.

However, although there are examples in which the proteins derived from the mammalian or microbial cells are expressed in the plants (Giddings, G. et al. (2000) Nat. Biotecnol., 18, 1151-1155; Daniell, H. et al. (2001) Trends Plant Sci., 6, 219-226), conformation and a sugar chain structure required for keeping the function of the protein are different from those in the original organism, and thus, the produced protein often has not had the original function. For example, erythropoietin was expressed in tobacco BY-2 cells, but it had no physiological activity in vivo (Matsumoto, S. et al. (1995) Plant Mol. Biol., 27, 1163-1172).

In conventional technology, proteins derived from the mammalian or microbial cells have been expressed in the plants, and the proteins themselves have been primarily extracted and utilized. It has been scarcely reported that the proteins derived from the mammalian or microbial cells have been expressed in the plants and a substance is produced in the plant by taking advantage of the protein expressed in the plant.

As the substance production in the plants, it has been reported that human $\beta$-1,4-galactosyltransferase was expressed in tobacco BY-2 cells and consequently galactose was newly bound by $\beta$-1,4 bond to the sugar chain of the glycoprotein conventionally present (Palacpac, N. Q. et al. (1999) Proc. Natl. Acad. Sci. USA, 96, 4692-4697). However, this reaction is the reaction in which one sugar is transferred from one sugar nucleotide using the glycosyltransferase, and is quite different from the reaction in which a macromolecule such as the hyaluronic acid is generated by transferring two types of sugar from types of sugar nucleotides in several thousand times.

The hyaluronic acid synthase has generally multiple transmembrane or membrane-associated domains. When the foreign gene is expressed in the host, in the membrane-bound protein such as hyaluronic acid synthase, the transmembrane or membrane-associated domains can not often keep the correct structure. For example, it has been suggested that in the active hyaluronic acid synthase, one hyaluronic acid synthase protein and about 14 to 18 molecules of cardiolipin which is a one of the common phospholipids present on the membrane form a complex to affect the hyaluronic acid synthase activity (Tlapak-Simmons, V. L. (1999) J. Biol. Chem., 274, 4239-4245). This way, it is predicted that it is considerably difficult to express in the plant the hyaluronic acid synthase which the plant does not naturally have.

Although the technology by which the hyaluronic acid is produced in the plant is anticipated to be highly useful, the hyaluronic acid is the foreign carbohydrate that the plants are incapable of producing, and it has been considered from the conventional technology that it is considerably difficult to produce in the plants the substance which the plants do not produce naturally and to produce the macromolecular substance as the hyaluronic acid.

The present invention primarily intends to express the hyaluronic acid synthase in the plants and produce the hyaluronic acid which is not naturally produced in the plants using plant cells or the plants.

DISCLOSURE OF THE INVENTION

Figure 1:
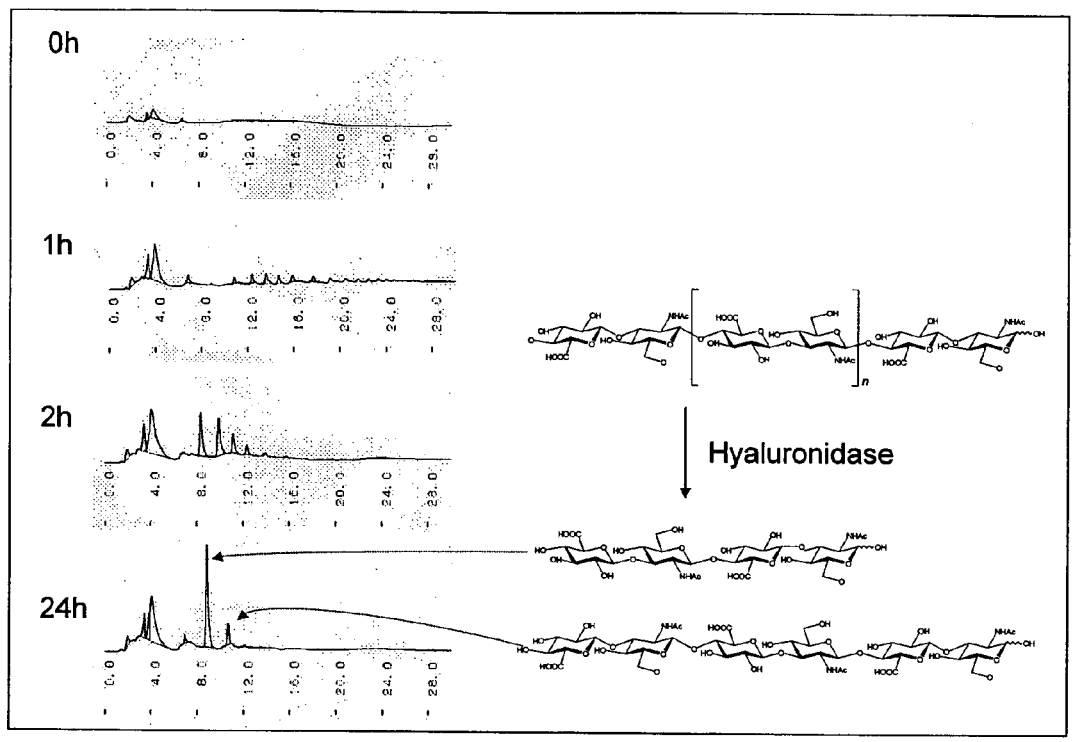
FIG. 1 is a HPLC profile of hyaluronan oligosaccharides mixture produced after hyaluronidase digestion.

As a result of an extensive study for solving the above problems, the present inventor has found that an active enzyme for synthesizing hyaluronic acid is expressed in plant cells or plants by transforming the plant cells or the plants with a DNA encoding a hyaluronic acid synthase or a DNA encoding a polypeptide having an activity of synthesizing the hyaluronic acid, further the hyaluronic acid is produced in the plants, by further extensively studying, and have completed the present invention.

That is, the present invention relates to the followings.

[1] A method of producing hyaluronic acid comprising (1) a step of transforming a plant cell using an expression recombinant vector comprising (i) a DNA encoding hyaluronic acid synthase or (ii) a DNA encoding a polypeptide having an amino acid sequence having one or more amino acid deletions, substitutions, additions or insertions in an amino acid sequence of the hyaluronic acid synthase and having an activity of synthesizing the hyaluronic acid, (2) a step of growing a transformant obtained by transformation, and (3) a step of separating the hyaluronic acid produced by the transformant.

[2] A method of producing hyaluronic acid comprising (1) a step of transforming a plant using an expression recombinant vector comprising (i) a DNA encoding hyaluronic acid synthase or (ii) a DNA encoding a polypeptide having an amino acid sequence having one or more amino acid deletions, substitutions, additions or insertions in an amino acid sequence of the hyaluronic acid synthase and having an activity of synthesizing the hyaluronic acid, (2) a step of growing a transformant obtained by transformation, and (3) a step of separating the hyaluronic acid produced by the transformant.

[3] A method of making a transformed plant cell having an ability of producing hyaluronic acid comprising a step of transforming a plant cell using an expression recombinant vector comprising (i) a DNA encoding hyaluronic acid synthase or (ii) a DNA encoding a polypeptide having an amino acid sequence having one or more amino acid deletions, substitutions, additions or insertions in an amino acid sequence of the hyaluronic acid synthase and having an activity of synthesizing the hyaluronic acid.

[4] A method of making a transformed plant having an ability of producing hyaluronic acid comprising a step of transforming a plant using an expression recombinant vector comprising (i) a DNA encoding hyaluronic acid synthase or (ii) a DNA encoding a polypeptide having an amino acid sequence having one or more amino acid deletions, substitutions, additions or insertions in an amino acid sequence of the hyaluronic acid synthase and having an activity of synthesizing the hyaluronic acid.

[5] The method according to [4] wherein the expression recombinant vector is the expression recombinant vector comprising (1) (i) the DNA encoding hyaluronic acid synthase or (ii) the DNA encoding the polypeptide having the amino acid sequence having one or more amino acid deletions, substitutions, additions or insertions in the amino acid sequence of the hyaluronic acid synthase and having the activity of synthesizing the hyaluronic acid and (2) an organ-specific or tissue-specific promoter, and the resulting transformed plant is the transformed plant having the ability of producing the organ-specific or tissue-specific hyaluronic acid.

[6] The method according any of [1] to [5] wherein the hyaluronic acid synthase is the hyaluronic acid synthase derived from a vertebrate or a microorganism.

[7] The method according any of [1] to [5] wherein the hyaluronic acid synthase is the hyaluronic acid synthase derived from chlorella virus.

[8] A transformed plant cell having an ability of producing hyaluronic acid, obtained by transforming a plant cell using an expression recombinant vector comprising (i) a DNA encoding hyaluronic acid synthase or (ii) a DNA encoding a polypeptide having an amino acid sequence having one or more amino acid deletions, substitutions, additions or insertions in an amino acid sequence of the hyaluronic acid synthase and having an activity of synthesizing the hyaluronic acid.

[9] A transformed plant having an ability of producing hyaluronic acid or a progeny thereof or an organ thereof or a tissue thereof having the same nature as in the plant, obtained by transforming a plant using an expression recombinant vector comprising (i) a DNA encoding hyaluronic acid synthase or (ii) a DNA encoding a polypeptide having an amino acid sequence having one or more amino acid deletions, substitutions, additions or insertions in an amino acid sequence of the hyaluronic acid synthase and having an activity of synthesizing hyaluronic acid.

[10] The transformed plant or the progeny thereof or the organ thereof or the tissue thereof having the same nature as in the plant according to [9] wherein the plant is the plant selected from the group consisting of angiosperm, gymnosperm, pteridophyte and bryophyte.

[11] The transformed plant or the progeny thereof or the organ thereof or the tissue thereof having the same nature as in the plant according to [9] wherein the organ is one or two or more organs selected from a root, a stem, a rootstock, a leaf, a flower, a root truncation, a seed and a shoot apex.

[12] The transformed plant or the progeny thereof or the organ thereof or the tissue thereof having the same nature as in the plant according to [9] wherein the tissue is one or two or more tissues selected from the group consisting of an epidermis, a phloem, a parenchyma, a xylem and a vascular bundle.

[13] The transformed plant or the progeny thereof or the organ thereof or the tissue thereof having the same nature as in the plant according to [9] wherein the expression recombinant vector is the expression recombinant vector comprising (1) (i) a DNA encoding hyaluronic acid synthase or (ii) a DNA encoding a polypeptide having an amino acid sequence having one or more amino acid deletions, substitutions, additions or insertions in an amino acid sequence of the hyaluronic acid synthase and having an activity of synthesizing hyaluronic acid and (2) a organ-specific or tissue-specific promoter, and the resulting transformed plant is the transformed plant having the ability of producing the organ-specific or tissue-specific hyaluronic acid.

[14] A transformed plant cell which produces hyaluronic acid synthase, obtained by transforming a plant cell using an expression recombinant vector comprising (i) a DNA encoding hyaluronic acid synthase or (ii) a DNA encoding a polypeptide having an amino acid sequence having one or more amino acid deletions, substitutions, additions or insertions in an amino acid sequence of the hyaluronic acid synthase and having an activity of synthesizing the hyaluronic acid.

[15] A transformed plant which produces hyaluronic acid synthase or a progeny thereof or an organ thereof or a tissue thereof having the same nature as in the plant, obtained by transforming a plant using an expression recombinant vector comprising (i) a DNA encoding hyaluronic acid synthase or (ii) a DNA encoding a polypeptide having an amino acid sequence having one or more amino acid deletions, substitutions, additions or insertions in an amino acid sequence of the hyaluronic acid synthase and having an activity of synthesizing the hyaluronic acid.

[16] The transformed plant cell according to [8] or [14] wherein the hyaluronic acid synthase is the hyaluronic acid synthase derived from a vertebrate or a microorganism.

[17] The transformed plant or the progeny thereof or the organ thereof or the tissue thereof having the same nature as in the plant according to any of [9] to [13] wherein the hyaluronic acid synthase is the hyaluronic acid synthase derived from a vertebrate or a microorganism.

[18] The transformed plant cell according to [8] or [14] wherein the hyaluronic acid synthase is the hyaluronic acid synthase derived from chlorella virus.

[19] The transformed plant or the progeny thereof or the organ thereof or the tissue thereof having the same nature as in the plant according to any of [9] to [13] wherein the hyaluronic acid synthase is derived the hyaluronic acid synthase from chlorella virus.

[20] A hyaluronic acid produced by the transformed plant cell according to [8] or [14] or the transformed plant or the progeny thereof or the organ thereof or the tissue thereof having the same nature as in the plant according to any of [9] to [13].

The present invention will be described in detail below.

In the present invention, a plant cell or a plant is transformed using a DNA encoding hyaluronic acid synthase or a DNA encoding a polypeptide having an amino acid sequence having one or more amino acid deletions, substitutions, additions or insertions in an amino acid sequence of the hyaluronic acid synthase and having an activity of synthesizing hyaluronic acid.

The source of the hyaluronic acid synthase is not particularly limited as long as the synthase synthesizes the hyaluronic acid having a polymer structure composed of a repeated structure of glucuronic acid and glucosamine using UDP-glucuronic acid and UDP-N-acetylglucosamine as substrates. For example, it is possible to use hyaluronic acid synthases derived from human, mouse, rabbit, chicken, cattle or *Xenopus laevis*, hyaluronic acid synthases derived from bacteria belonging to genera *Streptococcus* or *Passteurella*, hyaluronic acid synthase derived from chlorella virus and the like.

Among these hyaluronic acid synthases, the hyaluronic acid synthase derived from chlorella virus is particularly preferable.

The polypeptide having one or more amino acid deletions, substitutions, additions or insertions in the amino acid sequence of the hyaluronic acid synthase and having the activity of synthesizing the hyaluronic acid is the mutated polypeptide to an extent at which the activity of synthesizing the hyaluronic acid is not lost, and includes both the polypeptide which is a part of the hyaluronic acid synthase and has the activity of synthesizing the hyaluronic acid and the polypeptide which is the deletion, the addition, the insertion or the substitution of the hyaluronic acid synthase and has the activity of synthesizing the hyaluronic acid.

The polypeptide which is a part of the hyaluronic acid synthase and has the activity of synthesizing the hyaluronic acid is the polypeptide comprising amino acid sites essential for effecting the activity of synthesizing the hyaluronic acid in the above the hyaluronic acid synthase, deleting a part of unessential amino acid sites and having the activity of synthesizing the hyaluronic acid.

As one example of the polypeptide having one or more amino acid deletions, substitutions, additions or insertions in the amino acid sequence of the hyaluronic acid synthase and having the activity of synthesizing the hyaluronic acid, it has been reported that the hyaluronic acid synthase derived from *Passteurella multocida* has the activity of synthesizing the hyaluronic acid even when about 270 amino acid residues seemed to correspond to the transmembrane or membrane-associated domains have been deleted (Jing et al., 2000, Glycobiology, 10, 883-889).

Such mutations naturally occur and also include artificial mutations. The number of mutated amino acids are not limited as long as the activity of synthesizing the hyaluronic acid is not lost.

In the present invention, the DNA encoding the hyaluronic acid synthase or the DNA encoding the polypeptide having the amino acid sequence having one or more amino acid deletions, substitutions, additions or insertions in the amino acid sequence of the hyaluronic acid synthase and having the activity of synthesizing hyaluronic acid is not particularly limited as long as the DNA encodes the foregoing hyaluronic acid synthase or polypeptide, and the DNA having a different sequence due to degeneracy of codons is also included.

As such a DNA, publicly known hyaluronic acid synthase genes can be optionally used. For example, the hyaluronic acid synthase genes derived from human, mouse, rabbit, chicken, cattle *Xenopus laevis*, genera *Streptococcus, Passteurella*, and chlorella virus can be used.

More concretely, it is possible to use HAS1, HAS2 and HAS3 of the hyaluronic acid synthase (hHAS) gene derived from the human, HAS1, HAS2 and HAS3 of the hyaluronic acid synthase (mHAS) gene derived from the mouse, HAS1, HAS2 and HAS3 of the hyaluronic acid synthase (gHAS) gene derived from the chicken, HAS2 of the hyaluronic acid synthase (rHAS) gene derived from the rat, HAS2 of the hyaluronic acid synthase (bHAS) gene derived from the cattle, HAS1, HAS2 and HAS3 of the hyaluronic acid synthase (xHAS) gene derived from *Xenopus laevis*, the hyaluronic acid synthase (pmHAS) gene derived *Pasteurella multocida*, the hyaluronic acid synthase (spHAS) gene derived from *Streptococcus pyogenes*, the hyaluronic acid synthase (seHAS) gene derived from *Streptococcus equisimilis* and the HAS gene derived from chlorella virus PBCV-1 (cvHAS).

Some hyaluronic acid synthase (HAS) genes have various types such as HAS1, HAS2 and HAS3, and the types are not particularly limited.

Among them, the HAS gene derived from chlorella virus is particularly preferable.

The transformant of the present invention, in other words, the transformed plant cell or the transformed plant is made by transforming the plant cell or the plant using the expression recombinant vector comprising (i) the DNA encoding hyaluronic acid synthase or (ii) the DNA encoding the polypeptide having the amino acid sequence having one or more amino acid deletions, substitutions, additions or insertions in the amino acid sequence of the hyaluronic acid synthase and having the activity of synthesizing hyaluronic acid.

The transformed plant cell or the transformed plant of the present invention can be obtained by introducing the expression recombinant vector in which (i) the DNA encoding hyaluronic acid synthase or (ii) the DNA encoding the polypeptide having the amino acid sequence having one or more amino acid deletions, substitutions, additions or insertions in the amino acid sequence of the hyaluronic acid synthase and having the activity of synthesizing hyaluronic acid has been inserted into a host to transform so that an objective gene can be expressed.

Herein, the host means any of the whole plant, the seed, the plant organs (e.g., leaf, flower, stem, root, rootstock, etc.), the plant tissues (e.g., epidermis, phloem, parenchyma, xylem and vascular bundle, etc.), and cultured plant cells.

Herein, the plants mean multicellular plants including spermatophyte, pteridophyte, bryophyte and lichen, and include any of the whole plant, the seed, the plant organs (e.g., leaf, flower, stem, root, rootstock, etc.), the plant tissues (e.g., epidermis, phloem, parenchyma, xylem and vascular bundle, etc.), and cultured plant cells.

The hyaluronic acid is produced by culturing the transformant obtained by the transformation and separating the hyaluronic acid produced by the transformant.

As the expression recombinant vector, it is possible to use the vector usually used for making the transformed plant cell or the transformed plant.

Such a vector is not particularly limited as long as the vector comprises a promoter sequence capable of being transcribed in the plant cell and a polyadenylation site required for stabilization of a transcript. For example, plasmids, "pBI121", "pBI221", "pBI101", "pIG121Hm" and the like can be used.

When the cultured plant cell is used as the host, the transformation can be performed by introducing the expression recombinant vector in which (i) the DNA encoding hyaluronic acid synthase or (ii) the DNA encoding the polypeptide having the amino acid sequence having one or more amino acid deletions, substitutions, additions or insertions in the amino acid sequence of the hyaluronic acid synthase and having the activity of synthesizing hyaluronic acid has been inserted into the cultured plant cell by an electroporation method, a binary vector method of *Agrobacterium* or a particle bombardment. The plant cells in which the expression vector has been introduced are selected on the basis of resistance to antibiotics such as kanamycin. The transformed plant cells can be used for cell culture, tissue culture and organ culture, and it is also possible to reproduce the plant using a conventionally known plant tissue culture method.

Examples of the plant cells subjected to the transformation include BY-2 cells and T-13 cells derived from tobacco, kurodagosun cells derived from carrot, VR cells and VW cells derived from grape, PAR cells, PAP cells and PAW cells derived from *Phytolacca americana* L., T87 cells derived from *Arabidopsis*, Asp-86 cells, A. per cells, A. pas cells and A. plo cells derived from sparrowgrass, Cba-1 cells derived from water melon, Sly-1 cells derived from tomato, 1-Mar cells derived from mint, CRA cells and V208 cells derived from Madagascar periwinkle, Spi-WT cells, Spi-I-1 cells and Spi-12F cells derived from marsh grass, Lcy-1 cells, LcyD6 cells and LcyD7 cells derived from gourd, OS-1 cells derived from rice, Vma-1 cells derived from *Vinca rosea*, PSB cells, PSW cells and PSG cells derived from sesame, and ZE3 cells derived from *Zinnia elegans*.

When the plant, the plant organ or the plant tissue is used as the host, the transformation is performed by introducing the expression recombinant vector in which (i) the DNA encoding hyaluronic acid synthase or (ii) the DNA encoding the polypeptide having the amino acid sequence having one or more amino acid deletions, substitutions, additions or insertions in the amino acid sequence of the hyaluronic acid synthase and having the activity of synthesizing hyaluronic acid has been inserted into a collected plant section by the binary vector method of *Agrobacterium* or a particle bombardment or into protoplasts by the electroporation, and separating a tumorous tissue, a shoot or a hairy root obtained as a result of the transformation.

It is possible to directly use the tumorous tissue, the shoot or the hairy root obtained in this way for the cell culture, the tissue culture or the organ culture. It is also possible to reproduce the plant by administering plant hormone at an appropriate concentration using the conventionally known plant tissue culture method.

To reproduce the plants from the plant cells in which the hyaluronic acid synthase gene has been introduced, such plant cells may be cultured in a re-differentiating medium or a hormone-free MS medium. The transgenic plants can be made by transferring plantlets taking roots to soil and cultivating it. Methods of reproducing (re-differentiating) are different depending on types of the plant cells, but it is possible to optionally use the conventionally known plant tissue culture method.

For example, Fujimura et al's method (Fujimura et al., (1955), Plant Tissue Culture Lett., vol. 2:p74) can be used in the rice. Shillito et al' method (Shillito et al., Bio/Technology, vol. 7:p581, Gorden-Kamm, 1990, Plant Cell, 2, 603, 1989) can be used in maize. Visser et al' method (Visser et al., Theor. Appl. Genet, vol. 78:p589, 1989) can be used in potato. Nagata et al's method (Nagata et al., Planta 99, 12, 1971) can be used in the tobacco. Akama et al's method (Akama et al., Plant Cell Rep., vol. 12:p7) can be used in *Arabidopsis*.

The plants made by these methods or progenies thereof (reproductive media, e.g., the plants obtained from seeds, stem tubers and cut ears) having the same nature as in the plant are the subjects of the present invention.

When the enzyme having the activity of synthesizing the hyaluronic acid is expressed in the plant and further the hyaluronic acid is produced, accumulated or secreted in the plant, it is preferable to control the hyaluronic acid synthase gene such that the hyaluronic acid synthase is expressed specifically for an appropriate tissue or organ in the plant.

To perform such a control, the tissue-specific or organ-specific promoter may be further inserted in the expression recombinant vector.

Examples of the organ-specific promoter include a root-specific promoter, a rootstock-specific promoter, a leaf-specific promoter, a seed-specific promoter and a stem-specific promoter.

Examples of the tissue-specific promoter include a green tissue-specific promoter.

More concretely, as examples of usable promoters, the constitutively high expression promoter includes CaMV35S promoter which is the promoter of 35S RNA of cauliflower mosaic virus. The green tissue-specific promoter includes a promoter of rbs gene encoding a small subunit protein of ribulose-1,5-bisphosphate carboxylase, a promoter of CAB gene encoding a chlorophyll a/b bond protein, and a promoter of GapA gene encoding a glutaric aldehyde-3-phosphate dehydrogenase A subunit protein. The seed-specific promoter includes LOX promoter of lipoxygenase gene, Psl promoter of lectin gene, and AmylA promoter of amylase gene. The root-specific promoter includes A6H6H promoter of hyoscyamine 6b-hydroxylase gene and PMT promoter of putrescine N-methyltransferase. The stem-specific promoter includes a promoter of Sus4 gene of sucrose synthase and a promoter of patatin gene encoding a glycoprotein.

It is also thought to control the expression of the hyaluronic acid synthase gene with an induction promoter. Examples of the induction promoter will be described below.

PR1a promoter which is the disease resistance related gene promoter whose expression level is enhanced by injury or the addition of salicylic acid and rd29A gene promoter whose expression level is enhanced by dryness, low temperature, high concentration salt or conversion of abscisic acid are included. The promoter whose expression is induced by a compound used as an agricultural chemical includes a promoter of GST-27 gene encoding a 27 KDa subunit protein of glutathion S-transferase, whose expression is induced by a herbicide Safener, a kinase gene promoter and a PR gene protein promoter induced by benzo(1,2,3)-thiadiazole-7-carbothioic acid S-methylester (BTH). In addition, in order to more stably express the hyaluronic acid synthase gene in the plant cells, an insulator may be utilized, a signal peptide may be added to localize the hyaluronic acid synthase in the objective organelle, and a part of the hyaluronic acid synthase may be substituted or deleted.

The plants subjected to the transformation include all plants capable of introducing the gene.

The plants or the plant bodies of the present invention include monocotyledon and dicotyledon of angiosperm, and gymnosperm. Such plants include optional useful plants, particularly crop plants, vegetable plants, flower plants and woody plants.

The plants or the plant bodies of the present invention also include pteridophyte and bryophyte.

Examples of plant species usable in the present invention concretely include plants belonging to families of Solanaceae, Gramineae, Cruciferae, Rosaceae, Leguminosae, Cucurbitaceae, Labiatae, Liliaceae, Chenopadiaceae, Umbeliferae, Myrtaceae, and Convolvulaceae.

Examples of plants belonging to Solanaceae include the plants belonging to genus *Nicotiana, Solanum, Datura, Lycopersion* or *Petunia*, and include, for example, tobacco, eggplant, potato, tomato, red pepper and petunia.

Examples of plants belonging to Gramineae include the plants belonging to genus *Oryza, Hordeum, Secale, Sccharum, Echinochloa* or *Zea*, and include rice, barley, rye, cockspur, corn and maize.

Examples of plants belonging to Cruciferae include the plants belonging to genus *Raphanus, Brassica, Arabidopsis,* *Wasabia* or *Capsella*, and include oriental radish, cole, *Arabidopsis*, Japanese horseradish and nazuna.

Examples of plants belonging to Rosaceae include the plants belonging to genus *Orunus, Malus, Pynus, Fragaria* or *Rosa*, and include Japanese apricot, peach, apple, pear, strawberry plant and rose.

Examples of plants belonging to Leguminosae include the plants belonging to genus *Glycine, Vigna, Phaseolus, Pisum, Vicia, Arachis, Trifolium, Alphalfa* or *Medicago*, and include soy bean, adzuki bean, butter bean, pea, field bean, peanut, clover, and bur clover.

Examples of plants belonging to Cucurbitaceae include the plants belonging to genus *Luffa, Cucurbita* or *Cucumis*, and include gourd, pumpkin, cucumber and melon.

Examples of plants belonging to Labiatae include the plants belonging to genus *Lavadula, Mentha* or *Perilla*, and include lavender, mint and Japanese basil.

Examples of plants belonging to Liliaceae include the plants belonging to genus *Allium, Lilium* or *Tulipa*, and include Welsh onion, garlic, lily and tulip.

Examples of plants belonging to Chenopadiaceae include the plants belonging to genus *Spinacia*, and include marsh grass.

Examples of plants belonging to Umbeliferae include the plants belonging to genus *Angelica, Daucus, Cryptotaenia* or *Apitum*, and include shishiudo, carrot, honewort and celery.

Examples of plants belonging to Convolvulaceae include the plants belonging to genus *Ipomoea*, and include sweet potato.

The progenies having the same nature as in the above transformed plants or the organs thereof or the tissues thereof are also the subjects of the present invention.

The transformed plant cells which produce the hyaluronic acid synthase are included in the present invention. The transformed plants which produce the hyaluronic acid synthase or the progenies thereof or the organs thereof or the tissues thereof having the same nature as in the plant are also included.

The transformed plant cells which produce the hyaluronic acid synthase can be obtained by transforming the plant cells using the expression recombinant vector comprising (i) the DNA encoding hyaluronic acid synthase or (ii) the DNA encoding the polypeptide having the amino acid sequence having one or more amino acid deletions, substitutions, additions or insertions in the amino acid sequence of the hyaluronic acid synthase and having the activity of synthesizing the hyaluronic acid.

The transformed plant which produce the hyaluronic acid synthase can be obtained by transforming the plant using the expression recombinant vector comprising (i) the DNA encoding hyaluronic acid synthase or (ii) the DNA encoding the polypeptide having the amino acid sequence having one or more amino acid deletions, substitutions, additions or insertions in the amino acid sequence of the hyaluronic acid synthase and having the activity of synthesizing the hyaluronic acid.

In the transformed plant cells or plants, the hyaluronic acid synthase gene is expressed as the enzyme having the activity of synthesizing the hyaluronic acid.

It becomes possible to produce the hyaluronic acid in the plant by using the transformed plant cells or the transformed plant having the ability of producing the hyaluronic acid, or using the transformed plant cells or the transformed plant which produce the hyaluronic acid synthase.

Methods of separating or acquiring the hyaluronic acid produced by the transformed plant cells or the transformed plant include, for example, the following methods.

The transformed plant cell or the transformed plant is cultured and the hyaluronic acid is produced in the plant, and subsequently, the hyaluronic acid is optionally extracted from the transformed plant cell or the transformed plant by the method known publicly.

For example, in the case of the transformed plant, dried leaves of the plant are disrupted and extracted by an appropriate organic solvent.

An extract solution containing the hyaluronic acid is filtrated, and a filtrate solution of the hyaluronic acid containing no plant cell is obtained. This solution is purified by diafiltration to remove impurities with low molecular weight. It is possible to separate the hyaluronic acid by the diafiltration of the filtrate solution containing the dissolved hyaluronic acid with purified water followed by continuously discarding the filtrate. When pharmaceutical products are required, a step of precipitating nucleic acids from the solution may be further performed. This step can be performed by adding a cation surfactant such as quaternary ammonium compounds of cetylpyridinium chloride.

The hyaluronic acid acquired by the present invention can be utilized usefully for components of cosmetics and pharmaceuticals or biomaterials. Concretely, the hyaluronic acid can be used usefully as a moisture component in cosmetics or therapeutic agents for arthritis, rheumatoid arthritis, burn injury and cut injury, or a component of eyedrops.

According to the present invention, the hyaluronic acid which has not been naturally produced in the plant is produced in the plant. According to the present invention, the hyaluronic acid synthase is expressed in the plant, and further the hyaluronic acid is produced in the plant.

As a host system for producing the protein through genetic manipulation, it is possible to currently use genetically modified plants, cultured plant cells, cells from microorganisms such as *Escherichia coli* and yeast, cultured mammalian cells and genetically modified animals. However, all production systems have good and bad points, and it is necessary to select the optimal system in consideration of intended uses, properties and production amounts of the objective recombinant protein. Looking at the production systems other than the plant, in *Escherichia coli*, no processing of the protein occurs, inclusion bodies are likely formed, and decomposition by protease occurs which are problematic. In yeast, the sugar chain is modified, but the modification is inherent in the yeast. When the therapeutic substance is produced in the microorganism, the purification cost becomes extremely expensive in order to prevent endotoxin from contaminating. For the mammalian cells, it is difficult to maintain the cells, and expensive media are required. Additionally, the production on a large scale is difficult because growth rate is slow. Furthermore, there is a risk to be contaminated with virus and oncogene. In the case of the genetically modified animals, there are ethical problems in addition to maintenance issues.

Meanwhile, for the cultured plant cells and the plant in the plant production system, there are problems of a long development period and alkaloid, but conventional agricultural production systems can be used, scale-up is easy, and it is possible to produce the objective substance inexpensively in a large amount. There is also no concern of toxin and infectious virus which are problematic in the case of using the microorganism or the mammalian cell as the host. Thus, the cultured plant cell and the plant are promising substance production systems.

The hyaluronic acid production system by the plant in the present invention is the industrially advantageous production system because the safety is higher and the cost and energy load are smaller compared with the conventional production systems by mammalian or microbial cells.

Until now in the plant production system, even when the protein derived from the mammalian or microbial cells is expressed, since the genetic background is different, the conformational structure and the sugar chain structure required are not maintained, and thus the produced protein has often had no original function thereof. Conventionally, the protein derived from the mammalian or microbial cells has been expressed in the plant, and the protein itself has been extracted and utilized. However, it has been scarcely reported that the protein (enzyme) derived from the mammalian or microbial cells has been expressed in the plant and the substance is produced in the plant utilizing the enzyme expressed in the plant as in the present invention. It has been reported that the sugar structure was converted in the sugar chain structure which the plant naturally had in the plant in which glycosyltransferase derived from the human had been recombinated. In this case, the structure of the sugar chain which the plant had naturally produced was changed. Conventionally, there has been no actual example in which the substance which the plant has not produced at all is produced in the plant as the hyaluronic acid of the present invention. Furthermore, there is no example in which the macromolecular substance such as hyaluronic acid where two types of the sugars are repeated in the certain order several thousand times is produced in the plant.

The hyaluronic acid synthase has generally multiple transmembrane or membrane-associated domains. When the foreign membrane-bound protein such as hyaluronic acid synthase is expressed in the host, the transmembrane or membrane-associated domains can not often maintain the correct conformation. Particularly, it has been suggested that in the active hyaluronic acid synthase, one hyaluronic acid synthase protein and about 14 to 18 molecules of cardiolipin which is a one of the common phospholipids present on the membrane form a complex to affect the hyaluronic acid synthase activity. Therefore, it is beyond conventional expectation that the hyaluronic acid synthase which the plant does not naturally have is expressed in the plant and that the conformation in which the hyaluronic acid can be produced is maintained.

This way, the plant producing the hyaluronic acid in the present invention is the technology which can not be predicted from the conventional technology and achieves industrially extremely advantageous effects.

BEST MODE FOR CARRYING OUT THE INVENTION

The present invention will be described more concretely with reference to the following Examples, but the invention is not limited thereto.

EXAMPLES

1. Isolation of Hyaluronic Acid Synthase Gene Derived from Chlorella Virus

PCR primers were made in order to isolate a chlorella virus hyaluronic acid synthase gene (cvHAS) by PCR. The primers were designed with reference to sequence information of chlorella virus genome already shown (Kutish et al, 1996, Virology, 223, 303-317) (Li et al, 1995, Virology, 212, 134-150) (Li et al, 1997, Virology, 237, 360-377) (Lu et al, 1995, Virology, 206, 339-352) (Lu et al, 1996, Virology, 216, 102-123) and identification information of the hyaluronic acid synthase gene derived from chlorella virus (DeAngelis et al, 1997, Science, 278, 1800-1803), and made by adding restriction enzyme sites required for introducing into an expression vector. As the restriction enzyme sites, NdeI site was added to the 5'-primer and XbaI site was added to the 3'-primer.

```
5'-primer
5' - GCC GCC GCA TAT GGG TAA AAA TAT     (SEQ ID NO:3)
AAT CAT AAT GGT TTC G - 3'

3'-primer
5' - CTT GCA GTC TAG ATC ACA CAG ACT     (SEQ ID NO:4)
GAG CAT TGG TAG -3'
```

For templates of PCR, genomic DNA of chlorella virus CVHI1 and CVKA1 strains (provided by Prof. Takashi Yamada, Department of Molecular Biotechnology, Graduate School of Advanced Science of Matter, Hiroshima University) were used.

PCR was performed using KOD-plus⁻ (Toyobo) as DNA polymerase by a reaction system of 94° C. for 2 minutes, 2 cycles (94° C. for 15 seconds, 40° C. for 30 seconds and 68° C. for 1 minute) and 25 cycles (94° C. for 15 seconds, 60° C. for 30 seconds and 68° C. for 1 minute). The resulting PCR fragment was inserted in expression vector (modified pBS) modified such that an initiation codon, an ATG site of β-galactosidase gene of pBluescript IIKS(+) (abbreviated as pBS) was the NdeI site. The inserted fragments were identified as a DNA sequence of cvHAS-HI (SEQ ID NO:1), the hyaluronic acid synthase gene derived from CVHI1 strain and a DNA sequence of cvHAS-KA (SEQ ID NO:2), the hyaluronic acid synthase gene derived from CVKA1 strain by using a DNA sequencer.

2. Expression of cvHAS in *Escherichia coli* and Extraction Thereof

*Escherichia coli* JM109 carrying cvHAS-HI or cvHAS-KA cultivated overnight at 37° C. in Luria-Bertani medium (LB: 10 g/L Polypeton, 5 g/L yeast extract and 5 g/L NaCl) containing 50 µg/mL ampicillin was inoculated in 50 mL of fresh LB medium (1:100) containing 50 µg/mL ampicillin, 0.2% glucose and 0.3 mM isopropyl-β-D-thiogalactopyranoside (IPTG). IPTG induction was carried out at 20° C. for 72 hours. IPTG-induced cells were harvested by centrifugation and resuspended in in 30 mL of buffer (containing 20 mM Tris-HCl (pH 7.5), 0.2 M NaCl, 1 mM EDTA, 1 mM benzamidine and 1 mM 2-mercaptoethanol (2-ME)), and homogenized. A membrane fraction containing cvHAS was extracted by centrifuging (12,000 rpm, 20 minutes) the disrupted microbial cells and performing ultracentrifugation of its supernatant (×100,000 g, one hour), and resuspended in 200 µL of the buffer (same as the above) to make a cvHAS extract solution.

3. Measurement of cvHAS Activity

The activity of synthesizing the hyaluronic acid was represented by synthesizing the hyaluronic acid in vitro using the extract solution of cvHAS produced in *Escherichia coli* and measuring a concentration of the hyaluronic acid in the reaction mixture. For in vitro synthesis of the hyaluronic acid, a reaction mixture containing 100 mM Tris-HCl (pH 7.0), 40 mM MgCl$_2$, 0.2 mM EGTA, 20 mM 2-ME, 0.1% BSA, 2 mM UDP-GlcA, 2 mM UDP-GlcNAc, 20% glycerol and 10 µL of HAS extract solution and adjusted to 50 µL of a total volume was reacted at 37° C. for 2 hours, 4 hours and 20 hours (O/N). The reaction mixture was heated at 90° C. for 3 minutes to terminate the reaction. After the centrifugation of the reaction mixture, the supernatant was used for the measurement of the hyaluronic acid.

A hyaluronic acid plate "Chugai" (Fujirebio, Inc.) using a measuring agent for the hyaluronic acid by a hyaluronic acid-binding protein was used for the measurement of the hyaluronic acid.

The hyaluronic acid plate "Chugai" is a sandwich binding type quantification method of the hyaluronic acid using the hyaluronic acid-binding protein. The hyaluronic acid in a sample is bound to the hyaluronic acid-binding protein immobilized on a microtiter plate, and then an enzyme-labeled hyaluronic acid-binding protein is bound thereto to form a sandwich. Subsequently, when tetramethylbenzidine (TMB) and hydrogen peroxide are added, TMB is oxidized by an action of peroxidase which is the labeled enzyme to develop a color. After adding a reaction stopping solution, the concentration of the hyaluronic acid in the sample can be assessed by measuring absorbance (A450) at a wavelength of 450 nm and a control wavelength of 620 nm using a microplate reader.

A standard curve was made using standard hyaluronic acid solutions attached in this kit, the concentration of the hyaluronic acid contained in the sample was determined by subtracting the absorbance of the solution (Mock) containing no hyaluronic acid from the absorbance of the sample (ΔA450), and was described as the hyaluronic acid concentration (HA concentration, ng/mL) in Table 1.

For the value of the hyaluronic acid synthase activity, the absorbance was converted by the following calculations for representing the amount of the synthesized hyaluronic acid as mole. The absorbance of the standard hyaluronic acid (concentration 100 ng/mL) was A, and the absorbance of each sample was B. Then, the total amount of the reaction solution was 50 µL. Thus, the activity of each hyaluronic acid synthase was calculated as $$B \times 100 \text{ ng/mL}/A \times 50 \text{ µL}/1000 = C \text{ ng/reaction time.}$$

The molecular weight of the component unit (GlcA-GlcNAc) of the hyaluronic acid is 398.35, and thus, the molecular weight of (GlcA-GlcNAc)n can be represented as 398.5Xn−18X (n−1). Accordingly, in the case of n=10, the molecular weight of (GlcA-GlcNAc)$_{10}$ is calculated as 398.8×10−18×(10−1)=3821.5 Da.

Therefore, molecules of GlcA incorporated in the hyaluronic acid for each reaction time period was calculated as C/3821.5Xn (n=10)×100 =D pmol The protein concentration in the extract solution was measured by Bio-Rad protein assay reagent (Bio-Rad) using BSA as the standard protein. The results were described as the protein amount in Table 1.

The activity of the hyaluronic acid synthase was represented as the HAS activity in Table 1 by calculating molecules (pmol) of GlcA incorporated in hyaluronic acid synthesized for one hour by 1 mg of the protein contained in the hyaluronic acid extract solution.

In Table 1, the extract solution derived from *Escherichia coli* transformed with the vector containing no hyaluronic acid synthase was represented as Mock. The extract solution of the hyaluronic acid synthase derived from *Escherichia coli* transformed with vector bearing the hyaluronic acid synthase gene derived from *Streptococcus pyogenes* was represented as spHAS. The extract solution of the hyaluronic acid synthase derived from *Escherichia coli* transformed with vector bearing the hyaluronic acid synthase gene derived from chlorella virus CVKA1 strain was represented as cvHAS-KA. Those obtained by repeating twice were represented as cvHAS-KA1 and cvHAS-KA2, respectively. The extract solution of the hyaluronic acid synthase derived from Escherichia coli transformed with vector bearing the hyaluronic acid synthase gene derived from chlorella virus CVHI1 strain was represented as cvHAS-HI. Those obtained by repeating twice were represented as cvHAS-HI1 and cvHAS-HI2, respectively.

A representation method of the HAS activity is the same as the methods represented in JP 200-4886 A, tano, N. and Kimata, K. (1996) J. Biol. Chem., 271, 9875-9878, Tlapak-Summons. L et al., (1999) J. Biol. Chem., 274, 4246-4253.

TABLE 1

Expression analysis of cvHAS in *Escherichia coli*

| Sample | Reaction time | A450 (Ave) | ΔA450 | HA Concentration (ng/ml) | HA Concentration (pmol-GlcA) | Protein amount* | HAS activity (pmol/mg-protein/h) |
|---|---|---|---|---|---|---|---|
| Mock | 2 hours | 0.035 | — | — | — | — | — |
|  | 4 hours | 0.059 | — | — | — |  | — |
| spHAS | 2 hours | 0.062 | 0.027 | 14.2 | 5,312 |  | 851 |
|  | 4 hours | 0.122 | 0.063 | 33.2 | 12,395 | 3.12 | 993 |
| cvHAS-KA1 | 2 hours | 0.045 | 0.010 | 5.3 | 1,967 |  | 426 |
|  | 4 hours | 0.090 | 0.031 | 16.3 | 6,099 | 2.31 | 660 |
|  | O/N | 0.231 | 0.172 | 90.5 | 33,841 |  | 732 |
| cVHAS-KA2 | 2 hours | 0.045 | 0.010 | 5.3 | 1,967 |  | 475 |
|  | 4 hours | 0.080 | 0.021 | 11.1 | 4,132 | 2.07 | 499 |
|  | O/N | 0.232 | 0.173 | 91.1 | 34,038 |  | 822 |
| cvHAS-HI1 | 2 hours | 0.094 | 0.059 | 31.1 | 11,608 |  | 3,120 |
|  | 4 hours | 0.150 | 0.091 | 47.9 | 17,904 | 1.86 | 2,406 |
|  | O/N | 0.117 | 0.058 | 30.5 | 11,411 |  | 1,534 |
| cvHAS-HI2 | 2 hours | 0.057 | 0.022 | 11.6 | 4,328 |  | 1,258 |
|  | 4 hours | 0.106 | 0.047 | 24.7 | 9,247 | 1.72 | 1,344 |
|  | O/N | 0.271 | 0.212 | 111.6 | 41,711 |  | 1,213 |

As shown in the results in Table 1, it is demonstrated that the products of the isolated genes have the activity of the hyaluronic acid synthase.

4. Construction of the Plant Expression Vector

Fragments of cvHAS-HI and cvHAS-KA were amplified by PCR with plasmid DNA containing cvHAS-HI or cvHAS-KA made and whose HAS activity had been demonstrated in the above 3 as the template using the PCR primers made by adding the restriction enzyme sites by PCR. As the 5'-PCR primer, the primer in which the restriction enzyme site DraI was added on the sequence of the modified pBS was designed, and as the 3'-primer, a region containing the restriction enzyme site ScaI in multicloning site of the modified pBS was used.

5'-Primer (SEQ ID NO:5): 5'-GTG TGG AAT TTA AAG CGG ATA ACA ATT TCA CAC AGG-3'.
3'-Primer (SEQ ID NO:6): 5'-GGG CGA ATT GGA GCT CCA CCG CGG-3'.

Subsequently, cvHAS was inserted into the vector pBI121 (Jefferson et al., 1987, EMBO J, 6, 3901-3907) for plant transformation by digesting pBI121 with SmaI and ScaI and digesting cvHAS to be inserted with DraI and ScaI.

By the above, pBI121 plasmid (pBI121cvHI) containing cvHAS-HI and pBI121 (pBI121cvKA) containing cvHAS-KA could be prepared.

5. Preparation of Competent Cells for Electroporation

For the competent cells for the electroporation, a single colony of *Agrobacterium tumefaciens* strain LBA4404 was inoculated in 5 mL of LB medium and cultured with shaking at 28° C. overnight. This culture medium was inoculated in 500 mL of the LB medium and cultured with shaking at 28° C. until a turbidity became 0.5 at 600 nm. Microbial cells were harvested by centrifuging (5000 rpm, 10 minutes, 4° C.) the culture medium and removing the supernatant. In order to wash the microbial cells, 500 mL of sterilized water was added to suspend the microbial cells, and again the microbial cells were harvested by centrifuging (5000 rpm, 10 minutes, 4° C.) and removing the supernatant. This manipulation was repeated twice. Subsequently, 20 mL of cooled sterilized 10% glycerol solution was added to a precipitate to suspend the microbial cells, and the microbial cells were collected by centrifuging (5000 rpm, 10 minutes, 4° C.) and removing the supernatant. Then, 3 mL of cooled sterilized 10% glycerol solution was added to the precipitate to suspend the microbial cells, and 40 μL of an aliquot was dispensed in a 1.5 mL centrifuging tube, which was frozen in liquid nitrogen and then stored at −80° C.

6. Introduction of cvHAS-HI and cvHAS-KA into *Agrobacterium* LBA4404 Strain

Plasmid DNA pBI121cvHI or pBI121cvKA was prepared and introduced into *Agrobacterium tumefaciens* strain LBA4404 by electroporation. A suspension in which 40 μL of *A. tumefaciens* LBA4404 competent cells for the electroporation and 1 μL of the expression plasmid (200 μg/mL) had been mixed was infused in a cuvette previously cooled on ice having 1 mm of a distance between electrodes, and pulse electric filed (1.8 kV, 25 μF, 200 Ω) was applied thereto. Immediately, 500 μL of SOC was added and the cells were cultured at 28° C. for 3 hours. Subsequently, the culture medium was applied on the LB plate medium containing kanamycin, and cultured at 25° C. for 3 days to yield *Agrobacterium* cells carrying pBI121cvHI or pBI121cvKA.

7. Infection of Cultured Tobacco Cells (BY-2) with *Agrobacterium* LBA4404 Carrying pBI121cvHI or pBI121cvKA

*Nicotiana tabacum* L. cv Bright Yellow 2 (sometimes abbreviated as BY-2, Nagata et al., 1981, Mol Gen Genet, 184, 161-165) was used as the cultured tobacco cells for transformation. Tobacco BY-2 cells were cultured according to Nagata et al's method (Nagata et al., 1981, Mol Gen Genet, 184, 161-165), and modified LS (Linsmaier and Skoog) medium (Linsmaier and Skoog, 1965, Physiol Plant, 18, 100-127) in which $KH_2PO_4$ and thiamine HCl had been increased to 370 mg/L and 1 mg/L, respectively and sucrose at a final concentration of 3% and 2,4-dichlorophenoxyacetic acid (2,4-D) at a final concentration of 0.2 mg/L had been added in LS medium was used.

The transformation of the tobacco BY-2 cells was performed essentially according to An's method (An, 1985, Plant Physiol, 79, 568-570). An *Agrobacterium* culture medium (100 μL) carrying pBI121cvHI or pBI121cvKA cultured in 5 mL of LB medium containing 50 mg/L of kanamycin at 28° C. overnight and 4 mL of a suspension of the tobacco BY-2 cells cultured for 4 days were placed in a petri dish, mixed thoroughly and co-cultured at 25° C. for two days in the dark. In order to remove *Agrobacterium*, the culture medium in the petri dish was transferred into a 50 mL centrifuge tube, 20 mL of modified LS medium containing 100 mg/L kanamycin and 250 mg/L carbenicillin was further added thereto, and the supernatant was removed by centrifugation (1000 rpm, 4 minutes). Immediately, 25 mL of fresh modified LS medium was added, and the cells were washed by centrifugation (1000 rpm, 4 minutes). This manipulation was repeated three times. The cultured cells from which *Agrobacterium* had been removed were transferred onto the modified LS medium containing 100 mg/L kanamycin, 250 mg/L carbenicillin and 0.3% gellan gum, and cultured in the dark. After 3 weeks, callused cells were transferred onto a new plate, and growing clones were selected. Finally, the colonies were transferred to 30 mL of the modified LS medium containing 100 mg/L kanamycin and 250 mg/L carbenicillin, and liquid culture was performed.

8. Production of cvHAS in Cultured Cells and Extraction Thereof

The cells were separated from the medium by centrifuging (1000 rpm, 20 minutes) 150 mL of the tobacco BY-2 cells grown in the modified LS medium for 7 days. The cells were suspended in 30 mL of buffer (containing 20 mM Tris-HCl, pH 7.5, 0.2 M NaCl, 1 mM EDTA, 1 mM benzamidine and 10 mM 2-ME), and homogenized. A membrane fraction containing cvHAS was extracted by centrifuging (12,000 rpm, 20 minutes) the disrupted microbial cell solution and performing ultracentrifugation of its supernatant (×100,000 g, one hour), and resuspended in 300 μL of the buffer (containing 20 mM Tris-HCl, pH 7.5, 0.2 M NaCl, 1 mM EDTA, 1 mM benzamidine and 10 mM 2-ME) to make a cvHAS extract solution.

9. Quantification of Hyaluronic Acid Produced by Cultured Cells

The medium separated from the cells after the above cell culture, the cvHAS extract solution and the cvHAS extract solution treated with hyaluronidase were used as samples for the quantification of hyaluronic acid produced by tobacco BY-2 cells. The measurement was performed for two strains of the tobacco BY-2 cells carrying cvHAS-HI and cvHAS-KA, respectively. The medium separated from the cells was concentrated to 2 times by lyophilization. Hyaluronidase digestion was performed by dissolving hyaluronidase (Sigma) derived from bovine testis in 100 mL phosphate buffer (pH 5.3) containing 150 mM NaCl at a concentration of 100 mg/mL, adding it into the cvHAS extract solution and incubating at 37° C. for 4 hours. After heating each sample at 90° C. for 3 minutes, the centrifugation (12,000 rpm, 10 minutes) was performed, and its supernatant was used for the quantification of hyaluronic acid. The quantification of hyaluronic acid was performed using the hyaluronic acid plate "Chugai" (Fujirebio, Inc.). The results are shown in Table 2.

In Table 2, the sample derived from BY-2 transformed with the vector containing the hyaluronic acid synthase derived from chlorella virus CVKA1 was represented as cvHAS-KA, and those obtained by repeating twice were represented as cvHAS-KA1 and cvHAS-KA2, respectively. The sample derived from BY-2 transformed with the vector containing the hyaluronic acid synthase derived from chlorella virus CVKHI1 was represented as cvHAS-HI, and those obtained by repeating twice were represented as cvHAS-HI1 and cvHAS-HI2, respectively. The measurement results of the standard hyaluronic acid solutions attached to the hyaluronic acid plate "Chugai"n (Fujirebio, Inc.) were described as "hyaluronic acid (standard)". The concentration in parenthesis represents the concentration of the hyaluronic acid in the standard hyaluronic acid solution.

TABLE 2

Quantification of hyaluronic acid produced by cultured cells

| Sample | | A450 | Hyaluronic acid concentration (ng/mL) |
|---|---|---|---|
| Medium | cvHAS-HI1 | 0.824 | 2,035 |
| | cvHAS-HI2 | 0.672 | 1,655 |
| | cvHAS-KA1 | 0.654 | 1,610 |
| | cvHAS-KA2 | 0.903 | 2,233 |
| cvHAS extract solution | cvHAS-HI1 | 0.332 | 805 |
| | cvHAS-HI2 | 0.300 | 725 |
| | cvHAS-KA1 | 0.285 | 688 |
| | cvHAS-KA2 | 0.357 | 868 |
| cvHAS extract solution digested with hyaluronidase | cvHAS-HI1 | 0.013 | — |
| | cvHAS-HI2 | 0.013 | — |
| | cvHAS-KA1 | 0.010 | — |
| | cvHAS-KA2 | 0.010 | — |
| Hyaluronic acid (standard) (0 ng/ml) | | 0.010 | — |
| Hyaluronic acid (standard) (100 ng/ml) | | 0.042 | — |
| Hyaluronic acid (standard) (200 ng/ml) | | 0.080 | — |
| Hyaluronic acid (standard) (500 ng/ml) | | 0.187 | — |

As shown in Table 2, it is demondtrated that each line of the tobacco BY-2 cells produces the hyaluronic acid.

10. Measurement of Activity of cvHAS Produced by Cultured Cells

The activity of synthesizing the hyaluronic acid was assessed by synthesizing the hyaluronic acid in vitro using cvHAS extract solution produced in plant cell culture and measuring the hyaluronic acid concentration in the reaction solution. For in vitro synthesis of the hyaluronic acid, a reaction mixture containing 100 mM Tris buffer (pH 7.0), 40 mM $MgCl_2$, 0.2 mM EGTA, 20 mM 2-mercaptoethanol, 0.1% BSA, 2 mM UDP-GlcA, 2 mM UDP-GlcNAc, 20% glycerol and 10 μL of HAS extract solution and adjusted to 50 μL of a total volume was reacted at 37° C. for 0 or 2 hours. After the reaction, the reaction mixture was heated at 90° C. for 3 minutes to terminate the reaction. After the centrifugation of the reaction mixture, the supernatant was used for the measurement of the hyaluronic acid. The hyaluronic acid plate "Chugai" (Fujirebio, Inc.) was used for the measurement of the hyaluronic acid by the hyaluronic acid-binding protein. The protein concentration in the HAS extract solution was measured by Bio-Rad protein assay reagent (Bio-Rad) using BSA as the standard protein. The results are shown in Table 3.

TABLE 3

Measurement of activity of cvHAS produced by tobacco BY-2 cells

| Sample | Reaction time | A450 (Ave) | ΔA450 | HA Concentration (ng/ml) | HA Concentration (pmol-GlcA) | Protein amount* | HAS activity (pmol/mg-protein/h) |
|---|---|---|---|---|---|---|---|
| cvHAS-HI1 | 0 hour | 0.332 | | | | | |
| | 2 hours | 0.475 | 0.143 | 358 | 133,829 | 24.2 | 2,765 |
| cvHAS-HI2 | 0 hour | 0.300 | | | | | |
| | 2 hours | 0.403 | 0.103 | 258 | 96,477 | 14.8 | 3,258 |
| cvHAS-KA1 | 0 hour | 0.285 | | | | | |
| | 2 hours | 0.475 | 0.190 | 475 | 177,567 | 32.8 | 2,707 |
| cvHAS-KA2 | 0 hour | 0.357 | | | | | |
| | 2 hours | 0.483 | 0.126 | 315 | 177,755 | 25.0 | 2,355 |

As shown in Table 3, it is demonstrated that cvHAS, both cvHAS-HI and cvHAS-KA produced in the cells have the activity of synthesizing the hyaluronic acid. It is suggested that the hyaluronic acid synthase derived from the other source can also synthesize the hyaluronic acid in the plant cells.

11. Preparation of Fraction Containing Hyaluronic Acid Produced by Transformed Cultured Tobacco Cells The cell suspension (150 mL) of transformed BY-2 grown in the modified LS medium containing kanamycin (100 mg/L) and carbenicillin (250 mg/L) for 10 days was centrifuged (1000 rpm, 20 minutes) and the supernatant medium was collected. This medium was ultrafiltrated (amicon YM-10) to concentrate to about one-forth, subsequently a two fold amount of ethanol was added, and a precipitate was collected by centrifugation. It was demonstrated that the fraction containing the hyaluronic acid had been obtained by dissolving the precipitate in water and detecting the hyaluronic acid in the dissolution by the hyaluronic acid plate. An equal volume of a hyaluronidase solution in which hyaluronidase (Sigma) derived from bovine testis had been dissolved in 100 mM phosphate buffer(pH 5.3) containing 150 mM NaCl was added to this fraction containing the hyaluronic acid to start a hyaluronidase reaction at a final concentration of 2 kU/mL at 37° C. After a certain time period, the reaction mixture was heated at 95° C. for 20 minutes to stop the reaction. The supernatant obtained by centrifuging the reaction mixture was subjected to high-performance liquid chromatography (HPLC) analysis. In HPLC, essentially according to Tawada et al's method (Tawada et al., 2002, Glycobiology, 12, 421-426), 50 μL of the sample was analyzed with an amino column YMC-Pack NH$_2$ (4.6 mm×15 cm) under constant flow (1 mL/min) at 50° C. using a 30-minutes linear gradient of 20-500 mM NaH$_2$PO$_4$ as a mobile phase, and detected by UV (210 nm). FIG. 1 shows HPLC profile of hyaluronan oligosaccharides mixture produced after hyaluronidase digestion.

One hour after starting the reaction, multiple sugar peaks presumed to correspond to a low molecular weight hyaluronic acid mixture produced by hyaluronidase digestion were detected. Along with time course of the treatment with hyaluronidase, the molecular weights of the low molecular weight hyaluronic acid mixture were shifted to a lower molecular weight. Twenty-four hours after starting the reaction, most peaks of the mixture at an early phase disappeared, and only tetrasaccharide and hexasaccharide which were the final products were detected. Such a degradation pattern of oligosaccharides observed along with the time course of the treatment with hyaluronidase was the same as that of the hyaluronidase digestion of the authentic hyaluronic acid, suggesting that the fraction extracted from the medium of BY-2 contained the high molecular weight hyaluronic acid.

12. Infection of Tobacco with *Agrobacterium* LBA4404 Strain Containing pBI121cvHI or pBI121cvKA The transformation of tobacco (*Nicotiana tabacum* SR-1) was performed according to a leaf disc method using *Agrobacterium* ("Plant Biotechnology II" edited by Yasuyuki Yamada and Yoshimi Okada, Tokyo Kagaku Dojin, 1991). Sterilized leaf discs of the tobacco were immersed for 3 minutes in the culture medium of *Agrobacterium* containing carrying pBI121cvHI or pBI121cvKA cultured in 5 mL of the LB medium containing 50 mg/L of kanamycin at 28° C. overnight. Extra microbial cells were then removed on filter paper. The leaf discs were placed in differentiation medium in which 3% sucrose, B5 vitamin, 1 mg/mL benzylaminopurine, 1 mg/mL naphthalene acetate and 0.3% gellan gum had been added to MS (Murashige and Skoog) inorganic salt (Murashige and Skoog, 1962, Physiol Plant, 15, 473) and pH had been adjusted to 5.7, and left stand in the dark at 28° C. for 2 days. The infected leaf discs were washed three times with sterilized water, and extra water was removed on the filter paper. Subsequently, the leaf discs were left stand in the differentiation medium containing kanamycin (100 mg/L) and claforan (250 mg/L), and callus formation was induced under the condition of 16 hour light at 25° C. Three weeks after starting the induction, morphologically normal shoot was selected, cut out in a state containing stems and leaves, and transferred into rooting medium (MS inorganic salt, 3% sucrose, B5 vitamin and 0.3% gellan gum, pH 5.7) containing kanamycin (100 mg/L) and claforan (250 mg/L) to induce rooting under the condition of 16 hour light at 25° C. After 2 weeks, the shoot taking roots was transferred to the fresh rooting medium, and multiple lines with growing stems and leaves were obtained.

13. Quantification of Hyaluronic Acid Produced by Transformed Tobacco

Leaves (about 100 mg) from 6 lines of the transformed tobacco obtained by the above infection with *Agrobacterium* were transferred to a 2 mL tube and suspended in 200 μL of buffer (containing 20 mM Tris-HCl pH 7.5, 0.2 M NaCl, 1 mM EDTA and 10 mM 2-ME), and 400 mg of zirconia beads (diameter 2 mm) were added thereto. The tobacco leaves were pulverized by shaking and agitating the tube using Bead Smash (Wakenyaku, BS-12) (2,500 rpm, 5 minutes). A solution after the pulverization was centrifuged (15,000 rpm, 10 minutes), and the supernatant was collected as a crude extract solution. The crude extract solution was diluted 10 times, and used as the sample for the measurement. The quantification of the hyaluronic acid was performed using the hyaluronic acid plate "Chugai" (Fujirebio, Inc.). The results are shown in Table 4. The same pulverization treatment was performed using leaves from a tobacco wild strain (wild) and mock (tobacco transformed with pBI121), which were used as a control. Since the hyaluronic acid was significantly detected in one line (No. 2) of cvHAS-KA, it has been also confirmed that the hyaluronic acid is also produced in the tobacco plant obtained by the transformation.

TABLE 4

Quantification of hyaluronic acid produced by transformed tobacco

| Sample | A450 | Hyaluronic acid concentration (ng/mL) |
|---|---|---|
| cvHAS-HI3, No. 1 | 0.062 | 0 |
| cvHAS-HI3, No. 2 | 0.054 | 0 |
| cvHAS-HI3, No. 3 | 0.054 | 0 |
| cvHAS-HI3, No. 4 | 0.052 | 0 |
| cvHAS-KA1, No. 1 | 0.083 | 0 |
| cvHAS-KA1, No. 2 | 0.780 | 4,211 |
| Mock | 0.068 | 0 |
| Wild | 0.057 | 0 |
| Hyaluronic acid standard (0 ng/mL) | 0.055 | — |
| Hyaluronic acid standard (20 ng/mL) | 0.090 | — |
| Hyaluronic acid standard (50 ng/mL) | 0.254 | — |
| Hyaluronic acid standard (100 ng/mL) | 0.337 | — |
| Hyaluronic acid standard (200 ng/mL) | 0.566 | — |
| Hyaluronic acid standard (500 ng/mL) | 0.840 | — |

14. Identification of cvHAS Transcription in Transformed Tobacco

Total RNA was extracted from the leaves of 6 lines of the transformed tobacco obtained by infection with *Agrobacterium* described above. The extraction of the total RNA was performed using RNeasy Plant Mini Kit (QIAGEN) according to an attached protocol. The leaves (100 mg) were transferred to a mortar cooled thoroughly by liquid nitrogen, and pulverized by a pestle in the liquid nitrogen to make powder. Immediately, pulverized cells were suspended in 450 µL of Buffer RFT containing 1% 2-mercaptoethanol, and agitated by a vortex mixer. This pulverized solution was transferred to QIAshredder spin column, and removal of cell debris and homogenate were performed by the centrifugation. A half amount of ethanol was added to the resulting supernatant of the pulverized solution, and transferred to RNeasy mini column. Thereafter, according to the protocol, washing and elution were sequentially performed to extract the total RNA. The same pulverization treatment was performed using leaves from a tobacco wild strain (wild) and mock (tobacco transformed with pBI121), which were used as a control.

Figure 2:
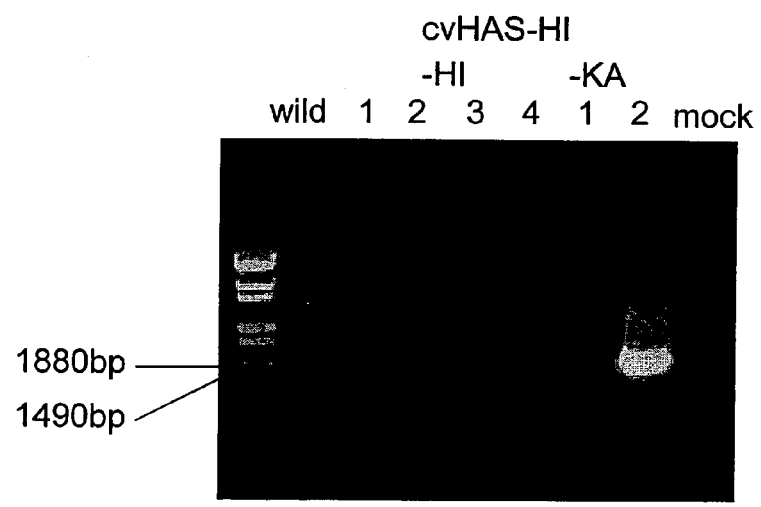
FIG. 2 is RT-PCR analysis for cvHAS in transformed tobacco leaves with agarose gel electrophoresis of DNA.

Subsequently, RT-PCR was performed using the above total RNA as the template. A 1st strand cDNA was synthesized using Rever Tra Ace-α⁻ (Toyobo) from 1 µg of the above total RNA and random primers according to the protocol. PCR with the 1st strand DNA as the template was performed using KOD Dash DNA polymerase (Toyobo) as the DNA polymerase by the reaction program of 30 cycles (95° C. for 30 seconds, 59 C for 2 seconds and 74 C for 30 seconds). As the primers, the 5'-primer (SEQ ID NO:3) and the 3'-primer (SEQ ID NO:4) were used. FIG. 2 shows the RT-PCR analysis for cvHAS in transformed tobacco leaves with agarose gel electrophoresis of DNA. A clear amplified band having a corresponding size was detected in only one line of cvHAS-KA in which the production of hyaluronic acid had been observed among the tobacco lines transformed with cvHAS, and the transcription of the cvHAS gene was identified.

The invention claimed is:

1. A method of producing hyaluronic acid comprising
   (1) a step of transforming a plant cell using an expression recombinant vector comprising
      (i) a DNA encoding hyaluronic acid synthase or
      (ii) a DNA encoding a polypeptide having an amino acid sequence of the hyaluronic acid synthase,
   (2) a step of growing a transformant obtained by transformation of step (1), and
   (3) a step of separating the hyaluronic acid produced by the transformant, wherein the hyaluronic acid synthase synthase is derived from a chlorella virus.

2. A method of producing hyaluronic acid comprising
   (1) a step of transforming a plant using an expression recombinant vector comprising
      (i) a DNA encoding hyaluronic acid synthase or
      (ii) a DNA encoding a polypeptide having an amino acid sequence of the hyaluronic acid synthase,
   (2) a step of growing a transformant obtained by transformation of step (1), and
   (3) a step of separating the hyaluronic acid produced by the transformant, wherein the hyaluronic acid is derived from a chlorella virus.

3. A method of making a transformed plant cell having an ability of producing hyaluronic acid comprising
   a step of transforming a plant cell using an expression recombinant vector comprising
   (i) a DNA encoding hyaluronic acid synthase or
   (ii) a DNA encoding a polypeptide having an amino acid sequence of the hyaluronic acid synthase,
   wherein the hyaluronic acid synthase is derived from a chlorella virus.

4. A method of making a transformed plant having an ability of producing hyaluronic acid comprising
   a step of transforming a plant cell using an expression recombinant vector comprising
   (i) a DNA encoding hyaluronic acid synthase or
   (ii) a DNA encoding a polypeptide having an amino acid sequence of the hyaluronic acid synthase,
   wherein the hyaluronic acid synthase is derived from a chlorella virus.

5. The method of claim 4 wherein the expression recombinant vector further comprises an organ-specific or tissue-specific promoter, wherein the resulting transformed plant has the ability of producing the organ-specific or tissue-specific hyaluronic acid.

6. A transformed plant cell having an ability of producing hyaluronic acid, obtained by transforming a plant cell using an expression recombinant vector comprising
   (i) a DNA encoding hyaluronic acid synthase or
   (ii) a DNA encoding a polypeptide having an amino acid sequence of the hyaluronic acid synthase,
   wherein the hyaluronic acid synthase is derived from a chlorella virus.

7. A transformed plant, or a progeny thereof or an organ thereof or a tissue thereof, having the ability of producing hyaluronic acid, wherein said plant is obtained by transforming a plant using an expression recombinant vector comprising
   (i) a DNA encoding hyaluronic acid synthase or
   (ii) a DNA encoding a polypeptide having an amino acid sequence of the hyaluronic acid synthase,
   wherein the hyaluronic acid synthase is derived from a chlorella virus.

8. The transformed plant or the progeny thereof or the organ thereof or the tissue thereof of claim 7, wherein the plant is selected from the group consisting of angiosperm, gymnosperm, pteridophyte and bryophyte.

9. The transformed plant or the progeny thereof or the organ thereof or the tissue thereof of claim 7, wherein the organ is one or more organs selected from the group consisting of a root, a stem, a rootstock, a leaf, a flower, a root truncation, a seed, and a shoot apex.

10. The transformed plant or the progeny thereof or the organ thereof or the tissue thereof of claim 7, wherein the tissue is one or more tissues selected from the group consisting of an epidermis, a phloem, a parenchyma, a xylem, and a vascular bundle.

11. The transformed plant or the progeny thereof or organ thereof or the tissue thereof of claim 7, wherein the expression recombinant vector further comprises an organ-specific or tissue-specific promoter, wherein the resulting transformed plant has the ability of producing the organ-specific or tissue-specific hyaluronic acid.

* * * * *